(12) United States Patent
Italiaie et al.

(10) Patent No.: US 11,712,270 B2
(45) Date of Patent: Aug. 1, 2023

(54) QUICK LOCK CLAMP CONSTRUCTS AND ASSOCIATED METHODS

(71) Applicant: Warsaw Orthopedic, Inc., Warsaw, IN (US)

(72) Inventors: Christel Italiaie, Memphis, TN (US); William A. Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 165 days.

(21) Appl. No.: 17/322,028

(22) Filed: May 17, 2021

(65) Prior Publication Data

US 2022/0361933 A1    Nov. 17, 2022

(51) Int. Cl.
*A61B 17/70*  (2006.01)
*A61B 17/86*  (2006.01)
*A61B 17/56*  (2006.01)

(52) U.S. Cl.
CPC ........ *A61B 17/7041* (2013.01); *A61B 17/704* (2013.01); *A61B 17/7034* (2013.01); *A61B 17/7035* (2013.01); *A61B 17/8685* (2013.01); *A61B 2017/564* (2013.01)

(58) Field of Classification Search
CPC .............. A61B 17/7035; A61B 17/704; A61B 17/7041
See application file for complete search history.

(56) References Cited

U.S. PATENT DOCUMENTS

| | | |
|---|---|---|
| 3,604,487 A | 9/1971 | Gilbert |
| 3,844,291 A | 10/1974 | Moen |
| 4,411,259 A | 10/1983 | Drummond |
| 5,020,519 A | 6/1991 | Hayes et al. |

(Continued)

FOREIGN PATENT DOCUMENTS

| | | |
|---|---|---|
| WO | 9855038 A1 | 12/1998 |
| WO | 0236026 A2 | 5/2002 |

(Continued)

OTHER PUBLICATIONS

European Search Report in Application No. 22163200.3 dated Sep. 16, 2022.

*Primary Examiner* — Julianna N Harvey
(74) *Attorney, Agent, or Firm* — Fox Rothschild LLP

(57) ABSTRACT

Disclosed implants may include a first implant receiver and a second implant receiver each having an upper portion and a lower portion connected together by an arm portion, for example. In various embodiments, the upper and lower portions may define a longitudinal passageway extending through the upper and lower portions in a longitudinal direction of each implant receiver, and the arm portions may each define a rod passageway extending in a lateral direction, for example. In various embodiments, each receiver may include a crown having an outside thread pattern threadably engaged within the longitudinal passageway and for mating with a corresponding nut having a similar interior thread pattern. In various embodiments, a rod may extend in the lateral direction through the rod passageways In various embodiments, in a non-tightened position, the rod may freely move and in a tightened position, the arms constrain the rod from moving.

19 Claims, 11 Drawing Sheets

(56) References Cited

U.S. PATENT DOCUMENTS

| | | | |
|---|---|---|---|
| 5,113,685 A | 5/1992 | Asher et al. | |
| 5,207,678 A | 5/1993 | Harms et al. | |
| 5,314,431 A | 5/1994 | Graziano | |
| 5,330,472 A | 7/1994 | Metz-Stavenhagen | |
| 5,364,397 A | 11/1994 | Hayes et al. | |
| 5,389,099 A | 2/1995 | Hartmeister et al. | |
| 5,449,361 A | 9/1995 | Preissman | |
| 5,458,608 A | 10/1995 | Wortrich | |
| 5,466,243 A | 11/1995 | Schmieding et al. | |
| 5,575,792 A | 11/1996 | Errico et al. | |
| 5,609,593 A | 3/1997 | Errico et al. | |
| 5,609,654 A | 3/1997 | Le et al. | |
| 5,616,143 A | 4/1997 | Schlapfer et al. | |
| 5,630,817 A | 5/1997 | Rokegem et al. | |
| 5,643,263 A | 7/1997 | Simonson | |
| 5,683,391 A | 11/1997 | Boyd | |
| 5,720,751 A | 2/1998 | Jackson | |
| 5,782,830 A | 7/1998 | Farris | |
| 5,797,911 A | 8/1998 | Sherman et al. | |
| 5,885,285 A | 3/1999 | Simonson | |
| 5,899,901 A | 5/1999 | Middleton | |
| 5,910,141 A | 6/1999 | Morrison et al. | |
| 5,944,720 A | 8/1999 | Lipton | |
| 5,947,967 A | 9/1999 | Barker | |
| 6,036,692 A | 3/2000 | Burel et al. | |
| 6,042,582 A | 3/2000 | Ray | |
| 6,063,088 A | 5/2000 | Winslow | |
| 6,074,391 A | 6/2000 | Metz-Stavenhagen et al. | |
| 6,280,442 B1 | 8/2001 | Barker et al. | |
| 6,415,693 B1 | 7/2002 | Simon et al. | |
| 6,440,133 B1 | 8/2002 | Beale et al. | |
| 6,497,166 B1 | 12/2002 | Fleckenstein | |
| 6,520,962 B1 | 2/2003 | Taylor et al. | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,755,830 B2 | 6/2004 | Minfelde et al. | |
| 6,857,343 B1 | 2/2005 | Easterbrooks et al. | |
| 6,872,209 B2 | 3/2005 | Morrison | |
| 6,945,933 B2 | 9/2005 | Branch et al. | |
| 7,066,939 B2 | 6/2006 | Taylor | |
| 7,226,453 B2 | 6/2007 | Chao et al. | |
| 7,572,264 B2 | 8/2009 | Null et al. | |
| 7,771,459 B2 | 8/2010 | von Oepen | |
| 7,846,167 B2 | 12/2010 | Garcia et al. | |
| 7,947,047 B2 | 5/2011 | Arnal | |
| 7,976,463 B2 | 7/2011 | Dewey et al. | |
| 7,988,699 B2 | 8/2011 | Martz et al. | |
| 8,048,124 B2 | 11/2011 | Chin et al. | |
| 8,100,916 B2 | 1/2012 | Kumar et al. | |
| 8,221,431 B2 | 7/2012 | Chenaux | |
| 8,231,635 B2 | 7/2012 | Sharifi-Mehr et al. | |
| 8,262,670 B2 | 9/2012 | Laubert et al. | |
| 8,343,165 B2 | 1/2013 | Berrevoets | |
| 8,394,108 B2 | 3/2013 | McLean et al. | |
| 8,459,155 B2 | 6/2013 | Canizares, Jr. et al. | |
| 8,460,307 B2 | 6/2013 | Saidha et al. | |
| 8,475,466 B2 | 7/2013 | Chenaux | |
| 8,540,756 B2 | 9/2013 | Olsen et al. | |
| 8,585,741 B2 | 11/2013 | Gabelberger et al. | |
| 8,747,411 B2 | 6/2014 | Mitchell | |
| 8,757,035 B2 | 6/2014 | Kerboul et al. | |
| 8,763,499 B2 | 7/2014 | Dahners | |
| 8,784,431 B1 | 7/2014 | Harder et al. | |
| 8,806,973 B2 | 8/2014 | Ross et al. | |
| 8,845,652 B2 | 9/2014 | Heinz | |
| 8,882,775 B2 | 11/2014 | LaPosta et al. | |
| 8,900,248 B2 | 12/2014 | Biyani | |
| 8,900,280 B2 | 12/2014 | Paroth et al. | |
| 8,932,303 B2 | 1/2015 | Bouliane | |
| 8,945,193 B2 | 2/2015 | Kirschman | |
| 8,951,264 B2 | 2/2015 | Saidha et al. | |
| 8,968,276 B2 | 3/2015 | Zemlok et al. | |
| 8,992,575 B1 | 3/2015 | Di Lauro et al. | |
| 8,992,587 B2 | 3/2015 | Kirschman | |
| 8,998,921 B2 | 4/2015 | Sharifi-Mehr et al. | |
| 9,017,333 B2 | 4/2015 | Beale et al. | |
| 9,055,943 B2 | 6/2015 | Zemlok et al. | |
| 9,089,371 B1 | 7/2015 | Faulhaber | |
| 9,113,976 B2 | 8/2015 | Yevmenenko et al. | |
| 9,138,279 B2 | 9/2015 | Laposta et al. | |
| 9,149,307 B2 | 10/2015 | Sandstrom et al. | |
| 9,216,044 B2 | 12/2015 | Nuckley et al. | |
| 9,265,540 B2 | 2/2016 | Kirschman | |
| 9,295,500 B2 | 3/2016 | Marigowda | |
| 9,314,274 B2 | 4/2016 | Amstutz et al. | |
| 9,387,025 B2 | 7/2016 | Santangelo et al. | |
| 9,402,663 B2 | 8/2016 | Peterson et al. | |
| 9,446,507 B2 | 9/2016 | Nino et al. | |
| 9,526,553 B2 | 12/2016 | Bess et al. | |
| 9,572,605 B2 | 2/2017 | Shipp | |
| 9,597,135 B1 | 3/2017 | Miller et al. | |
| 9,642,654 B2 | 5/2017 | Reimels et al. | |
| 9,649,139 B2 | 5/2017 | Sharifi-Mehr et al. | |
| 9,687,285 B2 | 6/2017 | Robinson | |
| 9,724,149 B2 | 8/2017 | Trieu et al. | |
| 9,808,354 B2 | 11/2017 | Willis et al. | |
| 9,820,740 B2 | 11/2017 | Zemlok et al. | |
| 9,855,087 B2 | 1/2018 | Divincenzo et al. | |
| 9,949,731 B2 | 4/2018 | Erramilli et al. | |
| 9,956,003 B2 | 5/2018 | Prevost | |
| 9,968,384 B2 | 5/2018 | Fischer et al. | |
| 9,987,066 B2 | 6/2018 | Stad et al. | |
| 10,045,787 B2 | 8/2018 | Krebs et al. | |
| 10,076,374 B2 | 9/2018 | Diduch et al. | |
| 10,105,165 B2 | 10/2018 | Biedermann et al. | |
| 10,117,684 B2 | 11/2018 | Saidha et al. | |
| 10,160,105 B2 | 12/2018 | Nino et al. | |
| 10,219,854 B2 | 3/2019 | Nino et al. | |
| 10,274,021 B2 | 4/2019 | Victor et al. | |
| 10,285,740 B2 | 5/2019 | May et al. | |
| 10,349,986 B2 | 7/2019 | Wall et al. | |
| 10,363,073 B2 | 7/2019 | Raina et al. | |
| 10,390,967 B2 | 8/2019 | Livorsi et al. | |
| 10,426,535 B2 | 10/2019 | Zander et al. | |
| 10,433,883 B2 | 10/2019 | DiVincenzo et al. | |
| 10,433,982 B2 | 10/2019 | Willis et al. | |
| 10,448,978 B2 | 10/2019 | Wall et al. | |
| 10,463,404 B2 | 11/2019 | Wall et al. | |
| 10,470,805 B2 | 11/2019 | Biedermann et al. | |
| 10,478,235 B2 | 11/2019 | Beale et al. | |
| 10,568,668 B2 | 2/2020 | Biedermann et al. | |
| 10,568,677 B2 | 2/2020 | DiVincenzo et al. | |
| 10,582,925 B2 | 3/2020 | Marks et al. | |
| 10,603,078 B2 | 3/2020 | Simpson et al. | |
| 10,639,080 B2 | 5/2020 | Sharifi-Mehr et al. | |
| 10,646,261 B2 | 5/2020 | Folger et al. | |
| 10,653,457 B2 | 5/2020 | Erramilli et al. | |
| 10,660,687 B2 | 5/2020 | Goodwin, Jr. et al. | |
| 10,682,167 B2 | 6/2020 | Sandstrom et al. | |
| 10,702,315 B2 | 7/2020 | Lindner | |
| 10,702,316 B2 | 7/2020 | Heuer | |
| 10,709,488 B2 | 7/2020 | Diduch et al. | |
| 10,729,419 B2 | 8/2020 | Diduch et al. | |
| 10,751,092 B2 | 8/2020 | Biedermann et al. | |
| 10,765,466 B2 | 9/2020 | Stad et al. | |
| 10,779,872 B2 | 9/2020 | Smith et al. | |
| 10,869,751 B2 | 12/2020 | Diduch et al. | |
| 10,874,448 B2 | 12/2020 | Rees et al. | |
| 2002/0166421 A1 | 11/2002 | Bowerman | |
| 2002/0169453 A1 | 11/2002 | Berger | |
| 2004/0049196 A1* | 3/2004 | Jackson | F16B 35/047 606/916 |
| 2005/0159750 A1 | 7/2005 | Doherty | |
| 2005/0273101 A1 | 12/2005 | Schumacher | |
| 2006/0041261 A1 | 2/2006 | Osypka | |
| 2006/0167455 A1* | 7/2006 | Clement | A61B 17/7037 606/264 |
| 2006/0241593 A1 | 10/2006 | Sherman et al. | |
| 2006/0241600 A1 | 10/2006 | Ensign et al. | |
| 2007/0010816 A1 | 1/2007 | Wilkinson et al. | |
| 2007/0122764 A1 | 5/2007 | Balfour et al. | |

(56) References Cited

U.S. PATENT DOCUMENTS

| | | |
|---|---|---|
| 2007/0161987 A1* | 7/2007 | Capote .............. A61B 17/704 606/86 A |
| 2008/0015596 A1 | 1/2008 | Whipple |
| 2008/0044196 A1 | 2/2008 | Companioni et al. |
| 2008/0071274 A1 | 3/2008 | Ensign |
| 2008/0147126 A1 | 6/2008 | Tipirneni et al. |
| 2008/0147128 A1 | 6/2008 | Fritzinger |
| 2008/0200918 A1 | 8/2008 | Spitler et al. |
| 2008/0215099 A1 | 9/2008 | Balfour et al. |
| 2008/0269768 A1 | 10/2008 | Schwager et al. |
| 2009/0005787 A1 | 1/2009 | Crall et al. |
| 2009/0264895 A1 | 10/2009 | Gasperut et al. |
| 2010/0249798 A1 | 9/2010 | Sournac et al. |
| 2010/0249846 A1 | 9/2010 | Simonson |
| 2011/0077693 A1 | 3/2011 | Yu |
| 2011/0137320 A1 | 6/2011 | von Oepen |
| 2011/0160775 A1 | 6/2011 | Carls et al. |
| 2011/0270321 A1 | 11/2011 | Prevost et al. |
| 2011/0270322 A1 | 11/2011 | Olsen et al. |
| 2011/0282398 A1 | 11/2011 | Overes et al. |
| 2011/0301650 A1 | 12/2011 | Johnson et al. |
| 2012/0123481 A1 | 5/2012 | Lin |
| 2012/0203288 A1 | 8/2012 | Lange et al. |
| 2012/0215263 A1 | 8/2012 | Lee |
| 2012/0239095 A1 | 9/2012 | Barrall |
| 2012/0253398 A1 | 10/2012 | Metcalf et al. |
| 2013/0072984 A1 | 3/2013 | Robinson |
| 2013/0072986 A1 | 3/2013 | Robinson |
| 2013/0184759 A1 | 7/2013 | Rinehart et al. |
| 2013/0261671 A1 | 10/2013 | Horvath |
| 2014/0018816 A1 | 1/2014 | Fenn et al. |
| 2014/0066945 A1 | 3/2014 | Humphreys et al. |
| 2014/0142639 A1 | 5/2014 | Vennard et al. |
| 2014/0172027 A1 | 6/2014 | Biedermann et al. |
| 2014/0257411 A1 | 9/2014 | Rezach |
| 2014/0288567 A1 | 9/2014 | Kroll |
| 2014/0324062 A1 | 10/2014 | Heuer et al. |
| 2015/0201972 A1 | 7/2015 | Doubler et al. |
| 2015/0201987 A1 | 7/2015 | Lemoine et al. |
| 2015/0250521 A1 | 9/2015 | Poker et al. |
| 2015/0359575 A1 | 12/2015 | Pech et al. |
| 2015/0374417 A1 | 12/2015 | Petit et al. |
| 2016/0278815 A1 | 9/2016 | Fitzpatrick |
| 2016/0317206 A1 | 11/2016 | Rezach et al. |
| 2017/0119537 A1 | 5/2017 | Tepper et al. |
| 2017/0245898 A1 | 8/2017 | May et al. |
| 2018/0049777 A1 | 2/2018 | Rezach |
| 2018/0070941 A1 | 3/2018 | Zemlok et al. |
| 2018/0071000 A1 | 3/2018 | Pham et al. |
| 2018/0110548 A1 | 4/2018 | May et al. |
| 2018/0146990 A1 | 5/2018 | Manzanares et al. |
| 2018/0153600 A1 | 6/2018 | Koller et al. |
| 2018/0193062 A1 | 7/2018 | May |
| 2018/0193063 A1 | 7/2018 | May |
| 2018/0206890 A1 | 7/2018 | Rezach |
| 2018/0235684 A1 | 8/2018 | Hawkes et al. |
| 2018/0353224 A1 | 12/2018 | Kam et al. |
| 2019/0076170 A1 | 3/2019 | Lehman, Jr. et al. |
| 2019/0159820 A1 | 5/2019 | Geist et al. |
| 2019/0175193 A1 | 6/2019 | Fenn et al. |
| 2019/0254729 A1 | 8/2019 | Rohlfing et al. |
| 2019/0254730 A1 | 8/2019 | Rohlfing et al. |
| 2019/0329388 A1 | 10/2019 | Erickson et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030015 A1 | 1/2020 | Grizzard et al. |
| 2020/0038064 A1 | 2/2020 | Stoklund et al. |
| 2020/0078056 A1 | 3/2020 | Biedermann et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0121397 A1 | 4/2020 | Elliott et al. |
| 2020/0121398 A1 | 4/2020 | Elliott et al. |
| 2020/0205805 A1 | 7/2020 | Marks et al. |
| 2020/0229849 A1 | 7/2020 | Biedermann et al. |
| 2020/0237412 A1 | 7/2020 | Erramilli et al. |
| 2020/0340558 A1 | 10/2020 | Riemhofer et al. |
| 2020/0375638 A1 | 12/2020 | Avidano et al. |
| 2020/0390478 A1 | 12/2020 | Rodriguez et al. |
| 2020/0390486 A1 | 12/2020 | Rodriguez et al. |

FOREIGN PATENT DOCUMENTS

| | | | |
|---|---|---|---|
| WO | 2007070757 A2 | 6/2007 | |
| WO | 2011057178 A1 | 5/2011 | |
| WO | WO-2011057178 A1 * | 5/2011 | ......... A61B 17/7004 |

* cited by examiner

QUICK LOCK CLAMP CONSTRUCTS AND ASSOCIATED METHODS

CROSS-REFERENCE TO RELATED APPLICATIONS

This application incorporates by reference U.S. Pat. No. 10,335,201, titled Spinal Implant System and Methods of Use, filed Jan. 25, 2017; U.S. Pat. No. 10,653,455 titled Spinal Implant System and Methods of Use filed Sep. 12, 2017; U.S. Pat. No. 6,790,209, titled Rod Reducer Instruments and Methods, filed Jul. 1, 2002; U.S. application Ser. No. 17/167,258, titled Instrument for locking Orthopedic Screws, filed Feb. 4, 2021; and U.S. application Ser. No. 17/104,897, titled Combination Set Screw Breakoff and Tab Breaker Instrument, filed Feb. 3, 2021. The entire contents of each are incorporated herein by reference.

FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods, spinal constructs, and bone fasteners can be delivered to a surgical site. The rods may be independently attached via a spinal construct and/or a plurality of spinal constructs to the exterior of two or more vertebral members. This disclosure describes an improvement over these prior technologies.

SUMMARY

The techniques of this disclosure generally relate to spinal constructs. In various embodiments, a spinal construct may include two implant receivers that may support a rod on the side thereof and clamp on to the rod to secure the rod relative to the implant receivers. Additionally, the implant receivers may be connected to a pair of bone screws, respectively. In some embodiments, a pair of implant receivers supporting a rod may be pre-assembled for rapid installation and/or ease of installation and the rod may optionally be pre-contoured.

In one aspect, the present disclosure provides for an implant. The implant may include a first implant receiver having a first upper portion and a first lower portion connected together by a first arm, for example. In various embodiments, the first upper portion and first lower portion define a first longitudinal passageway extending through the first upper portion and first lower portion in a longitudinal direction, and the first arm defines a first rod passageway extending in a lateral direction, for example. The implant may include a second implant receiver having a second upper portion and a second lower portion connected together by a second arm, for example. In various embodiments, the second upper portion and second lower portion define a second longitudinal passageway extending through the second upper portion and second lower portion in the longitudinal direction, and the second arm defines a second rod passageway extending in the lateral direction, for example. In various embodiments, a first crown having a first outside thread pattern extending along an outside circumferential surface of the first crown and having a size and shape corresponding to a size and shape of the first longitudinal passageway may be provided, for example. In various embodiments, a second crown having a second outside thread pattern extending along an outside circumferential surface of the second crown and having a size and shape corresponding to a size and shape of the second longitudinal passageway may be provided, for example. Additionally, a first nut having a first inside thread pattern extending along an inside circumferential surface of the first nut and having a size and shape corresponding to a size and shape of the first outside thread pattern may be provided, for example. Additionally, a second nut having a second inside thread pattern extending along an inside circumferential surface of the second nut and having a size and shape corresponding to a size and shape of the second outside thread pattern may be provided, for example. In various embodiments, a rod extending in the lateral direction through the first and second lateral passageways may be provided, for example. In various embodiments, in a non-tightened position, the rod may freely move in the lateral direction through the first and second lateral passageways, for example. In various embodiments, in a tightened position, the first nut and second nut are threadably engaged with the first crown and second crown, respectively, and the first arm and second arm directly contact and constrain the rod from moving in lateral direction and/or longitudinal direction.

In another aspect, a method for installing a spinal implant is disclosed. The method may include providing a pre-assembled implant that is at least partially assembled in advance of surgery at a manufacturing facility or in advance of surgery during pre-operative planning, for example. The pre-assembled implant may include a first implant receiver having a first upper portion and a first lower portion connected together by a first arm, for example. In various embodiments, the first upper portion and first lower portion define a first longitudinal passageway extending through the first upper portion and first lower portion in a longitudinal direction, and the first arm defines a first rod passageway extending in a lateral direction, for example. The implant may include a second implant receiver having a second upper portion and a second lower portion connected together by a second arm, for example. In various embodiments, the second upper portion and second lower portion define a second longitudinal passageway extending through the second upper portion and second lower portion in the longitudinal direction, and the second arm defines a second rod passageway extending in the lateral direction, for example. In various embodiments, a first crown having a first outside thread pattern extending along an outside circumferential surface of the first crown and having a size and shape corresponding to a size and shape of the first longitudinal passageway may be provided, for example. In various embodiments, a second crown having a second outside thread pattern extending along an outside circumferential surface of the second crown and having a size and shape corresponding to a size and shape of the second longitudinal passageway may be provided, for example. Additionally, a first nut having a first inside thread pattern extending along an inside circumferential surface of the first nut and having a size and shape corresponding to a size and shape of the first outside thread pattern may be provided, for example Additionally, a second nut having a second inside thread pattern extending along an inside circumferential surface of the second nut and having a size and shape corresponding to a size and shape of the second outside thread pattern may be provided, for example. In various embodiments, a rod extending in the lateral direction through the first and second lateral passageways may be provided, for example. The method may further include the step of securing first and second bone screws to a patient; and securing the pre-assembled spinal implant to the first and second bone screws, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
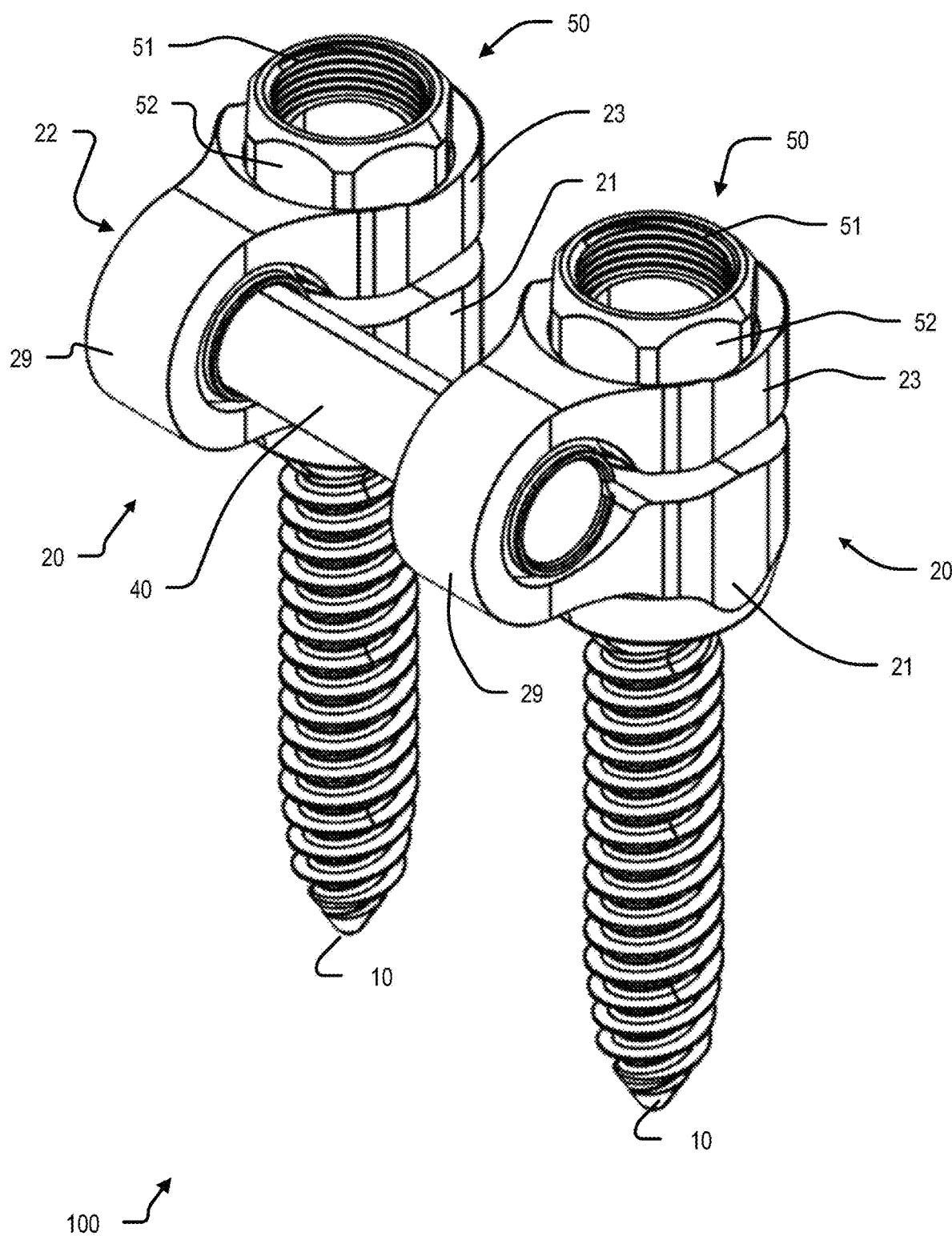
FIG. 1 is a perspective view of a spinal implant system.

Embodiments of the present disclosure relate generally, for example, to spinal stabilization systems, and more particularly, to side loading spinal constructs. In some embodiments, a side loading spinal construct may include two implant receivers that may support a rod and be connected to a pair of bone screws, respectively. In some embodiments, the two implant receivers and the rod may optionally be pre-assembled for rapid installation and/or ease of installation to the pair of bone screws. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-10 generally, various spinal implant systems 100 are disclosed. FIG. 11 discloses a method of use of various disclosed spinal implant systems 100. The components of spinal implant system 100 can be fabricated from biologically acceptable materials suitable for medical applications, including metals, synthetic polymers, ceramics and bone material and/or their composites. For example, the components of spinal implant system 100, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 100 may have material composites, including the above materials, to achieve various desired characteristics such as strength, rigidity, elasticity, compliance, biomechanical performance, durability and radiolucency or imaging preference. The components of spinal implant system 100, individually or collectively, may also be fabricated from a heterogeneous material such as a combination of two or more of the above-described materials, for example. The components of spinal implant system 100 may be monolithically formed, integrally connected or include fastening elements and/or instruments, as described herein.

Figure 2:
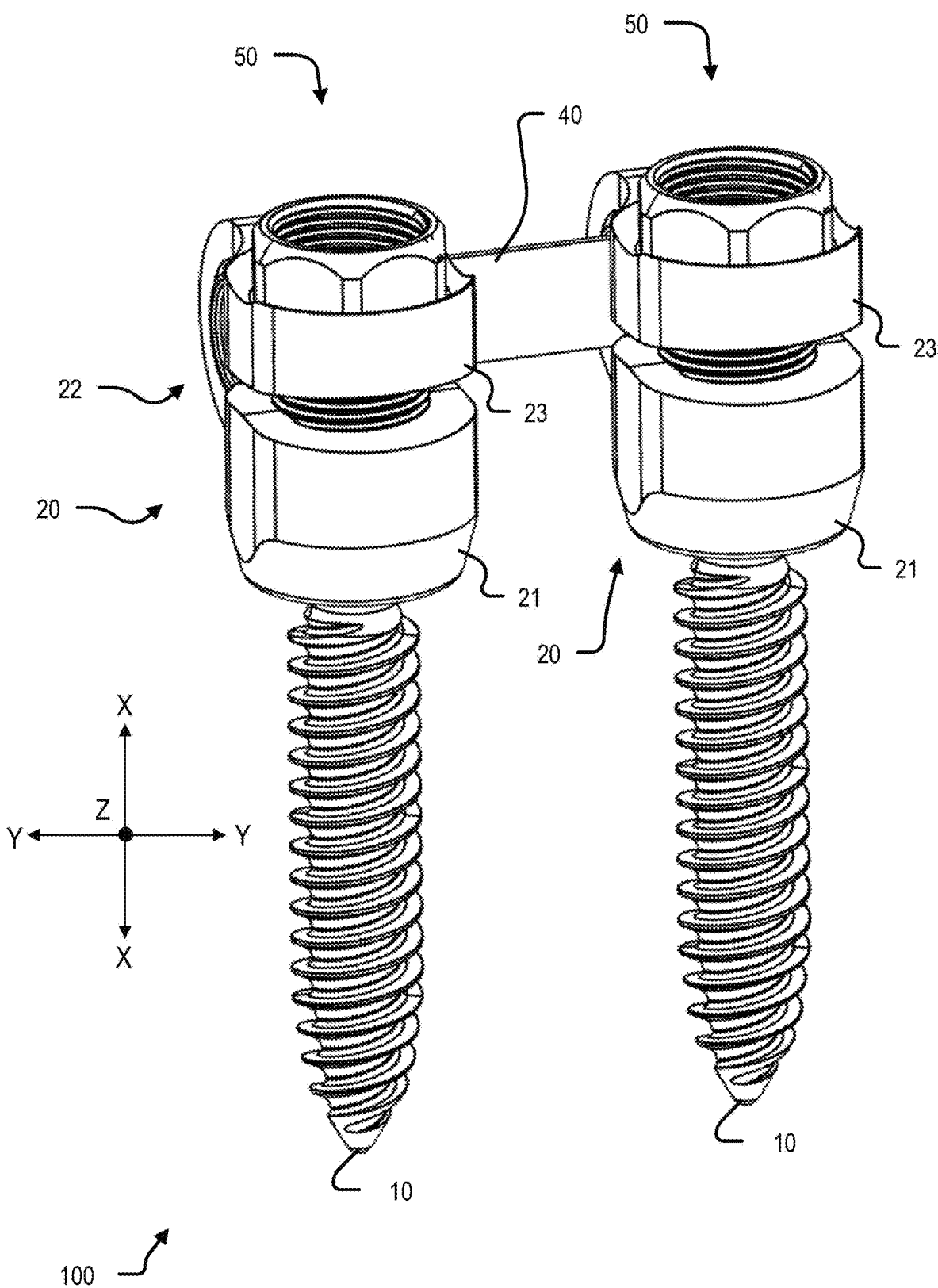
FIG. 2 is a side view of a spinal implant system.
Figure 3:
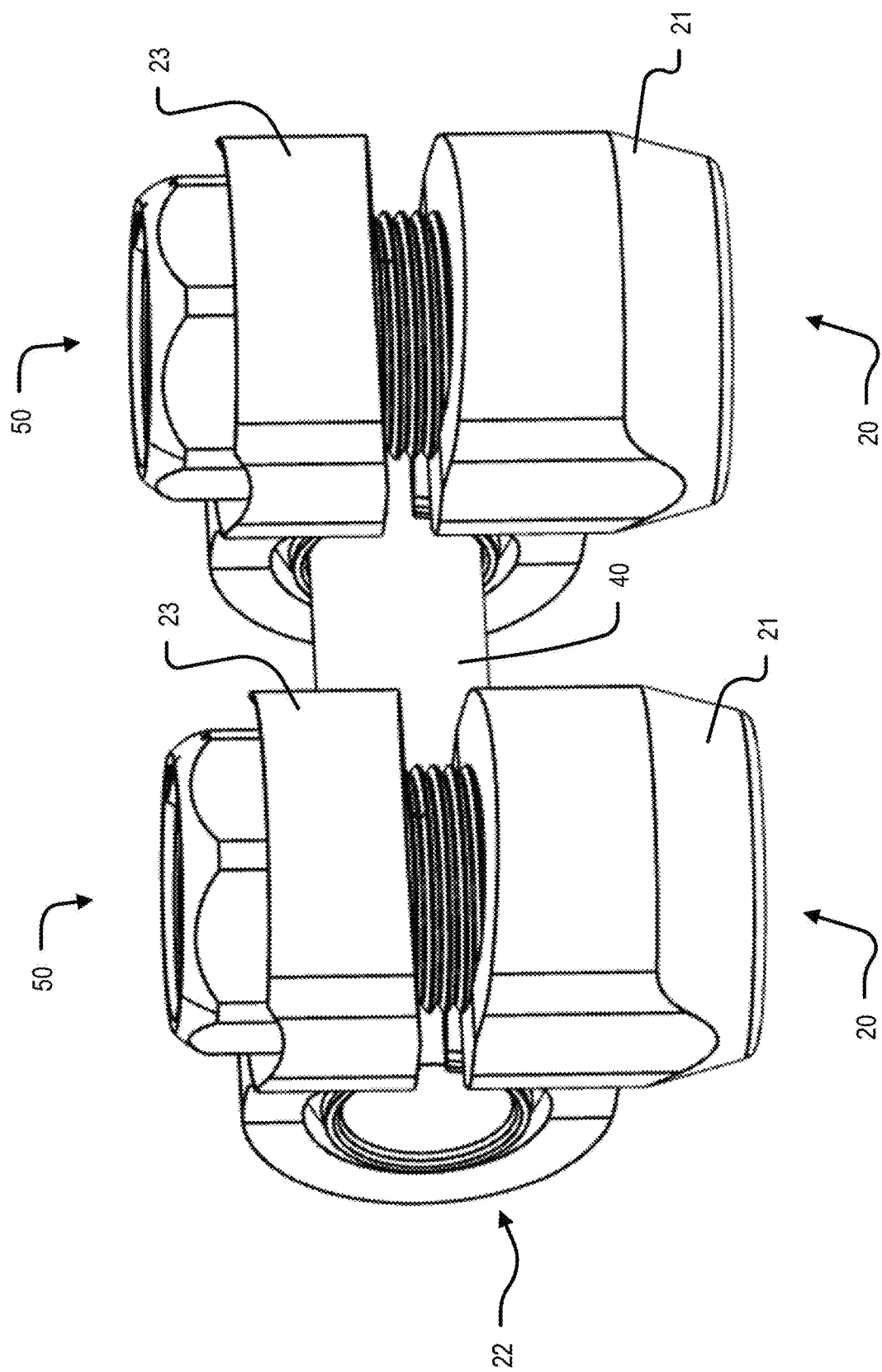
FIG. 3 is a perspective view of a pre-assembled portion of a spinal implant system.

FIG. 1 is a perspective view of a spinal implant system 100 and FIG. 2 is a side view of spinal implant system 100. Spinal implant system 100 may include a first implant receiver 20 and a second implant receiver 20. In the example embodiment, first and second implant receivers 20 are the same type of implant receiver. However, in other embodiments, first and second implant receivers 20 may be substantially the same, and or similar to one another. First and second implant receivers 20, may each include a passageway 22 for receiving a rod 40, for example. Additionally, first and second implant receivers 20 may include first and second nuts 50, respectively. Nuts 50 may move upward and downward in the vertical direction, labeled as X direction in FIG. 2, to secure rod 40 within passageway 22, for example. In some embodiments, nut 50 may be a breakoff setscrew having a breakoff portion, for example. In other embodiments, nut 50 may be a solid setscrew without a breakoff portion, for example. In the example embodiment, nut 50 includes an internal thread pattern 51 and an external drive surface 52. External drive surface 52 may include a plurality of radially disposed planar surfaces for driving nut 50 with a wrench, drive socket, or the like, for example.

Figure 8:
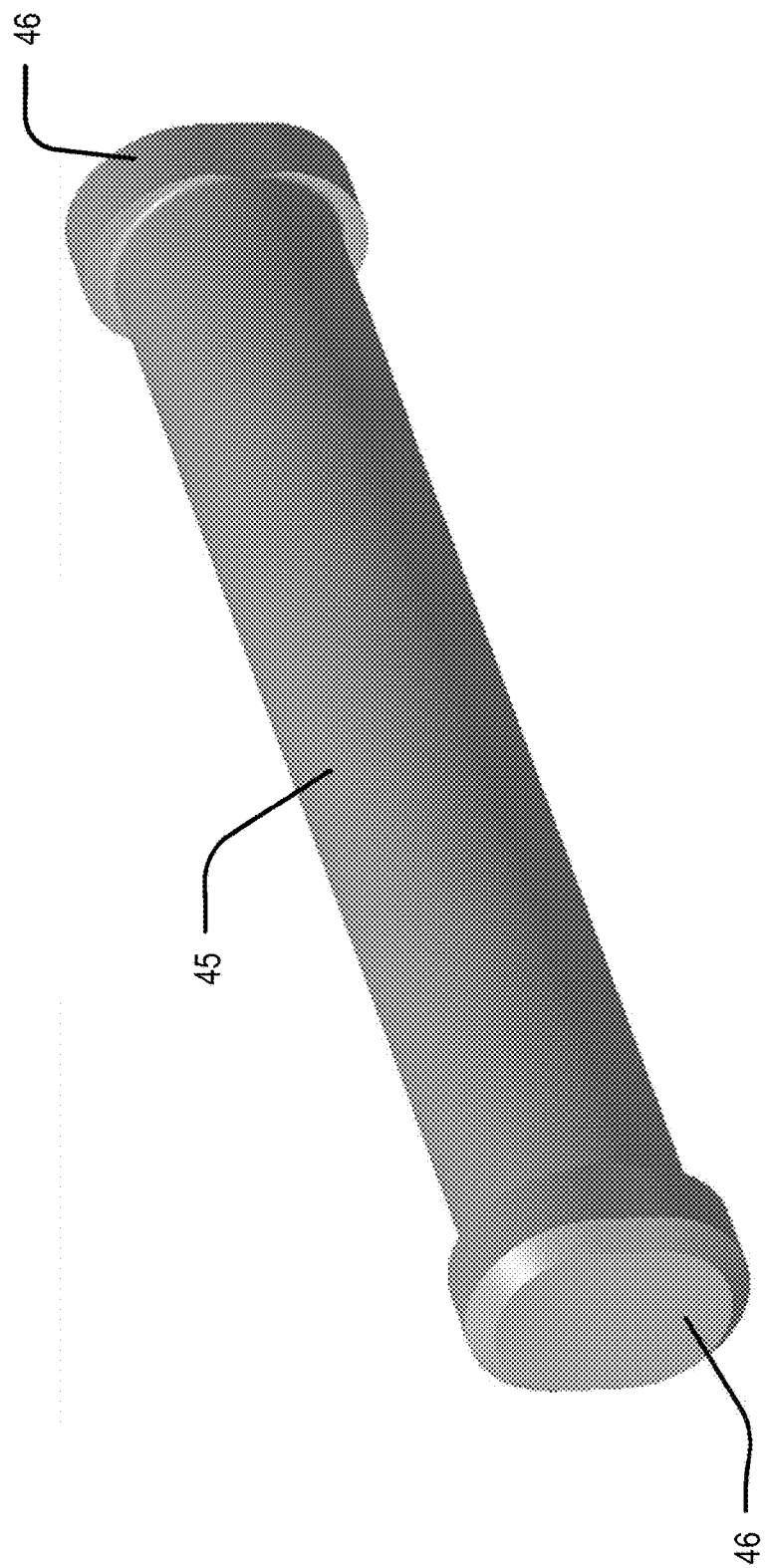
FIG. 8 is a perspective view of a rod for use with disclosed spinal implant systems.

In the example embodiment, each passageway 22 may comprise an aperture extending through the side of implant receiver 20. For example, passageways 22 of the first and second implant receivers 20 may be disposed on a side portion of implant receiver 20. For example still, implant receivers 20 may be side loading implant receivers. In the example embodiment, implant receivers 20 each include an upper portion 23 and a lower portion 21 that are connected together by arm 29. In various embodiments, arm 29 may comprise a C shaped portion adjoining the upper portion 23 and lower portion 21. In the example embodiment, an interior circumferential surface of arm 29 defines a passageway 22 for receiving a rod 40, for example. Passageway 22 may be closed at the upper end 23 of implant receiver 20 and lower end 21 of implant receiver 20 such that the rod 40 is confined within the passageway 22 in two dimensions. For example, in various embodiments, the passageway 22 may confine the rod 40 in the vertical direction (labeled as X direction in FIG. 2), and in the lateral direction (labeled as Z direction in FIG. 2) but still permit some sliding in the horizontal direction (labeled as Y direction in FIG. 2). For example, a perimeter of the passageway 22 is enclosed in the vertical direction and in the lateral direction due to the interior circumferential surface of arm 29. For example, as illustrated in FIG. 2, the rod 40 is confined in the vertical direction and in the lateral direction by passageway 22 but may permit movement in the horizontal direction. However, as shown in FIG. 8, some embodiments may utilize an alternate rod 45 having closed end caps 46, which may constrain rod 45 from moving too far in the horizontal direction and sliding out of passageway 22, for example.

Figure 4B:
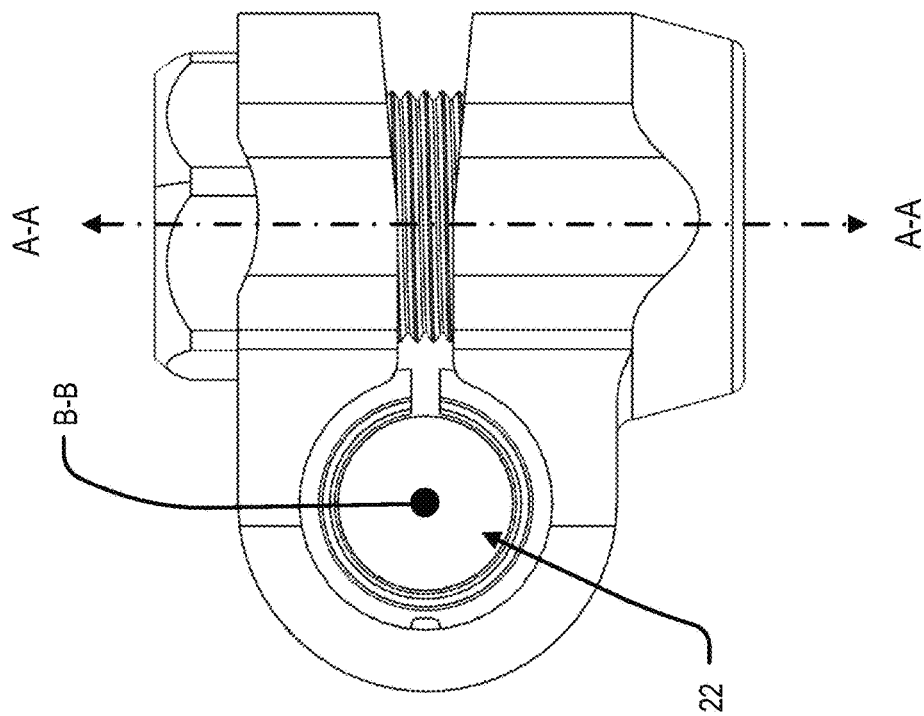
FIG. 4B is a top view of a receiver for use with disclosed spinal implant systems.
Figure 4A:
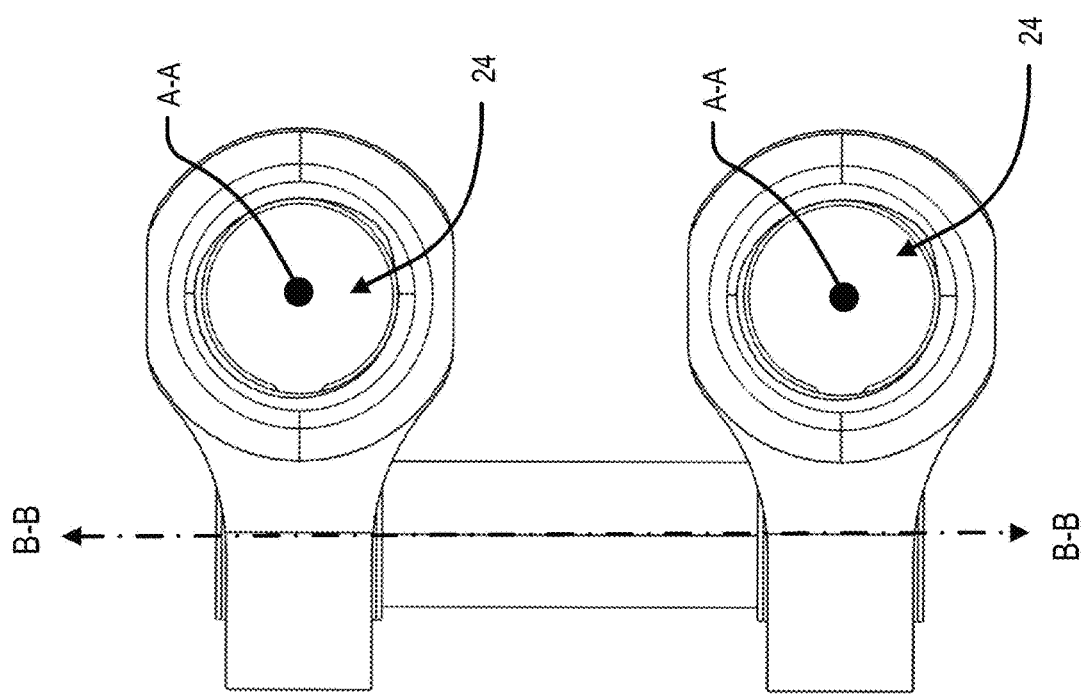
FIG. 4A is a side view of a receiver for use with disclosed spinal implant systems.

FIG. 4A is a top view of an implant receiver 20 and FIG. 4B is a side view of an implant receiver 20. In the example illustration, implant receiver 20 may include a passageway 24 for rotatably supporting and receiving a crown 2 and a nut 50, for example. Passageway 24 may be threaded at the lower portion 21 and/or upper portion 23, for example Passageway 24 may extend in the vertical direction (may also be referred to as longitudinal direction) and define a vertical axis A-A of which crown 2 and nut 50 may move upward and downward in upon rotation thereof. Additionally, implant receiver 20 may include a separate passageway 22 for receiving rod 40, for example. Passageway 22 may extend in the horizontal direction (may also be referred to as a lateral direction) and define a horizontal axis B-B, which rod 40 may be coaxially aligned with and/or extend in a substantially parallel direction with, for example. In various embodiments passageway 22 extends in a perpendicular direction to passageway 24. Additionally, in a plan view, passageway 22 may be disposed laterally outward to the side of passageway 24, for example. For example, passageway 22 is offset to the side of passageway 24 as illustrated in FIGS. 4A-4B by the offset nature of axes A-A and B-B. In the example embodiment, passageway 22 may resemble a circle and/or approximate a circle shape having an open end facing passageway 24. For example, passageway 22 may be a C shaped passageway having an internal diameter that accommodates a rod 40 and the C shaped passageway may be closed and/or narrowed by tightening of nut 50. In other embodiments, passageway 22 may resemble an oval and/or approximate an oval shape, or a square shape, for example. In various embodiments, passageway 22 may have a size and shape generally corresponding to a size and shape of rod 40, for example. For example, in an untightened position where nut 50 is not fully tightened a diameter of passageway 22 may be relatively large and permit rod 40 to freely move forward and backward through passageway 22. In a tightened position where nut 50 is fully tightened a diameter of passageway 22 may be relatively small and clamp onto rod 40 such that rod 40 is secured in place. In various embodiments, a side view cross section of rod 40 may have approximate an oval shape generally corresponding to a size and shape of passageway 22, for example.

Figure 5:
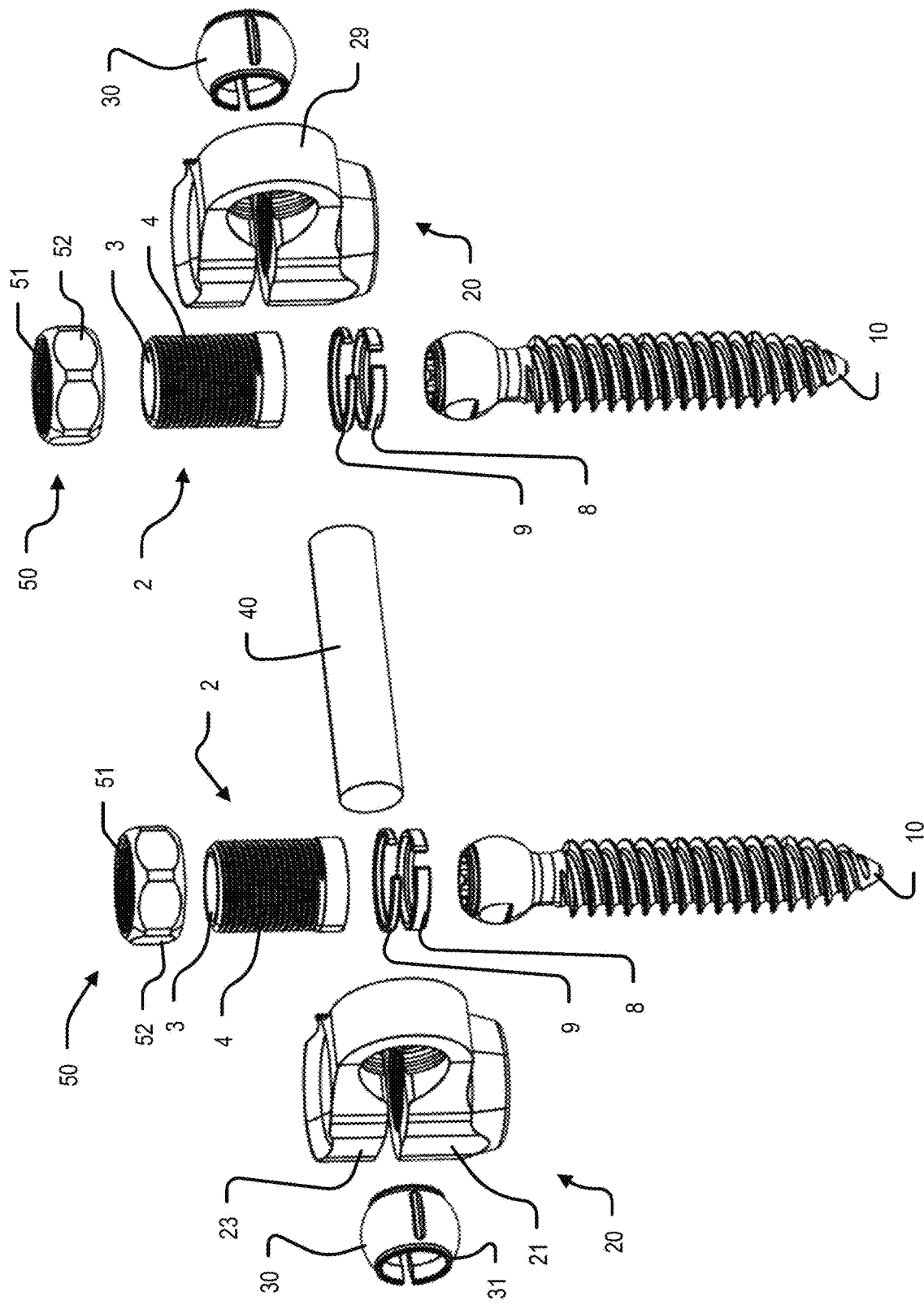
FIG. 5 is a perspective view exploded parts diagram of a spinal implant system.
Figure 6:
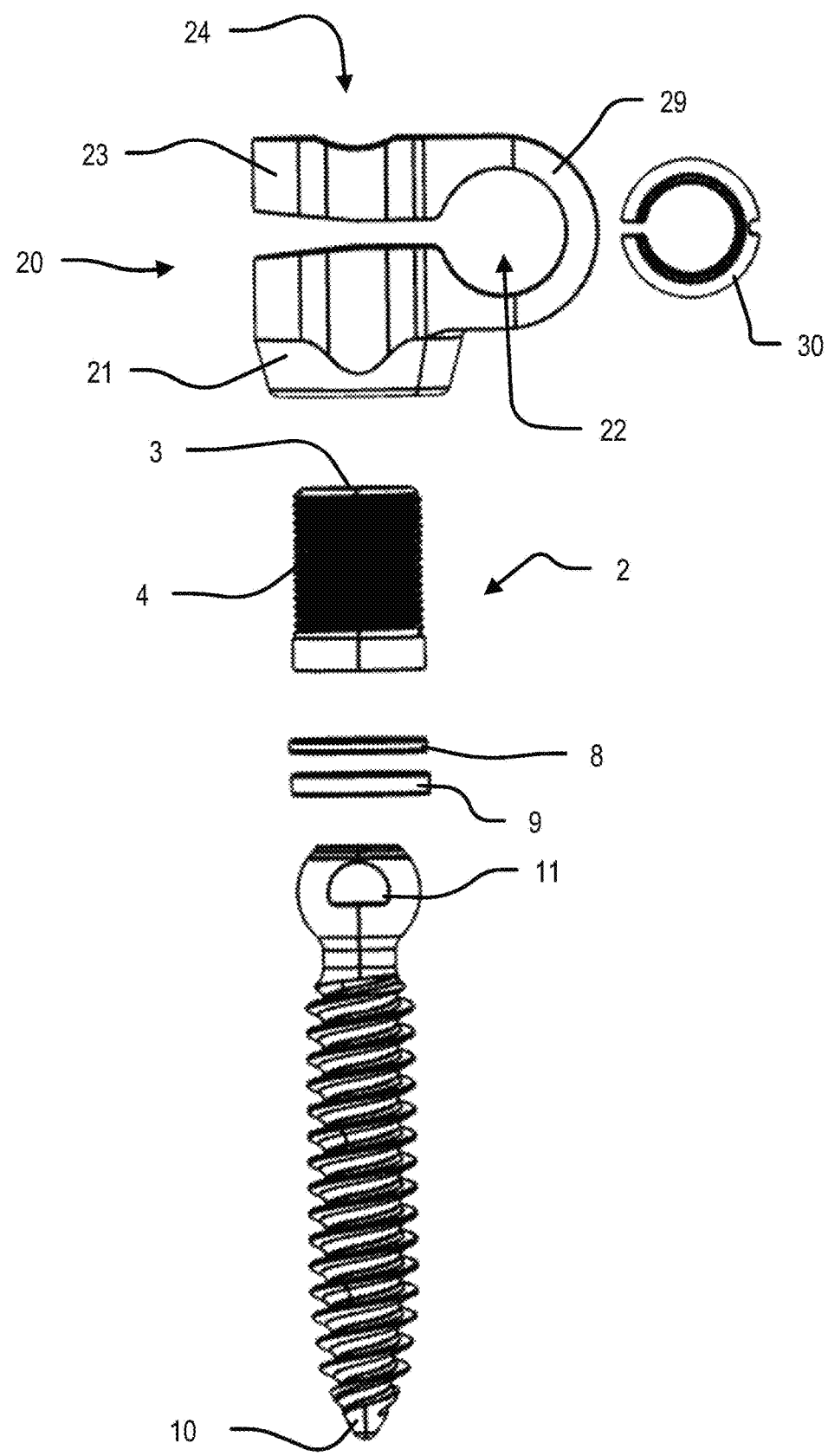
FIG. 6 is a perspective view exploded parts diagram of a receiver and various components for connecting to a bone screw.
Figure 7:
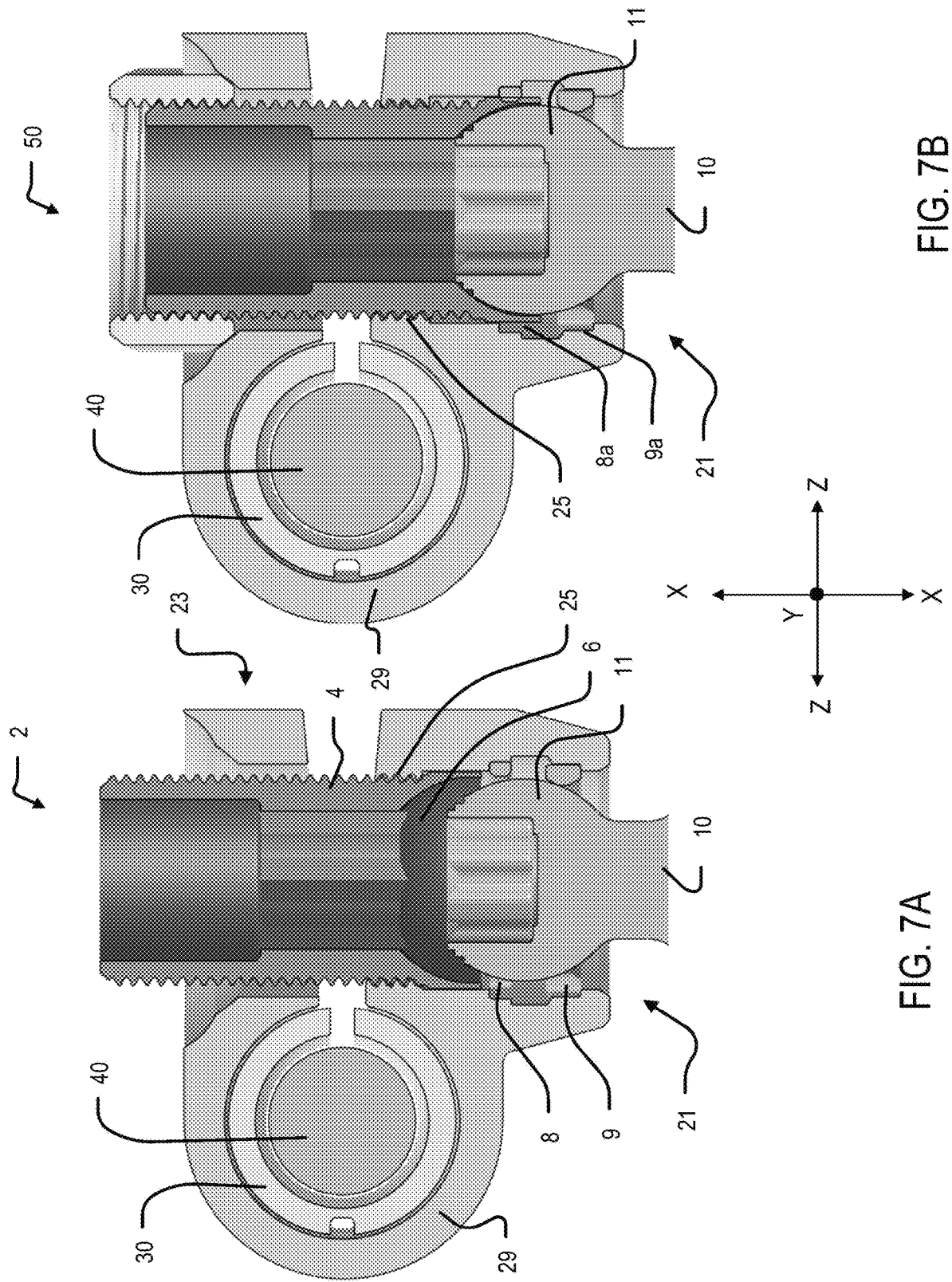
FIG. 7A is a side cross section view of a spinal implant system.
FIG. 7B is a side cross section view of a spinal implant system.

FIG. 5 is a side view exploded parts diagram of a spinal implant system 100 and FIG. 6 is a perspective view exploded parts diagram of a spinal implant system 100. In the example illustrations, it is shown that crown 2 may include an external thread pattern 4 and a drive aperture 3 for driving crown 2 through passageway 24 of implant receiver 20. For example, crown 2 may be insert within passageway 24 from above and be rotated by a drive tool which moves crown 2 downward through passageway 24. Drive aperture 3 may take any shape, for example a hexalobular shape, a hexaganol shape, a torx shape, etc. nut 50 may have an interior thread pattern 51 having a timing and/or pitch including a size and shape generally corresponding to the timing and or pitch of the external threads 4 of crown 2, for example. Additionally, nut 50 may include an internal thread pattern 51 and an external drive surface 52 for driving nut 50 with a drive tool (not illustrated) to rotate nut 50, for example. In various embodiments, the pitch and/or timing of the external thread pattern 4 of crown 2 may correspond to the pitch and/or timing of the internal thread pattern 51 of nut 50.

In operation, an end user may secure the first and second implant receivers 20 to first and second bone screws 10 by tightening crown 4 at drive aperture 3 such that crown 4 advances downward through passageway 24 along the vertical axis A-A and secures to a head portion of bone screw 10, for example. Thereafter, an end user may secure rod 40 within rod passageway 22 by securely tightening nut 50. For example, nut 50 may be rotated such that nut 50 advances downward along the outside thread pattern 4 of crown 2 such that nut 50 advances downward along the vertical axis A-A. In advancing nut 50 downward, nut 50 compresses and/or pushes the upper portion 23 and lower portion 21 towards one another. For example, because the upper portion 23 and lower portion 21 are adjoined on one end by arm portion 29 arm portion 29 allows the upper portion 23 and lower portion 21 to be pushed towards one another by an elastic deformation at arm portion 29.

FIG. 6 is a perspective view exploded parts diagram of an implant receiver 20 for use with disclosed spinal implant systems 100. In the example illustration, it is shown that implant receiver 20 may include a base portion 21 having a lower cavity configured to securely couple to bone screw 10 and support a crown 2 in a position above the head portion 11 of bone screw 10, for example. Crown 2 may include a threaded outer surface 4 which may engage with a corresponding interior thread pattern 25 of the base portion 21 (see FIGS. 7A and 7B). Spinal implant system 100 may further include an upper ring 8 and a lower ring 9. Upper and lower rings 8, 9 may be C-shaped and configured to securely couple head portion 11 of bone screw 10 within lower cavity of base portion 21, for example. Additional examples of how implant receiver 20 may securely connect to a bone screw 10 via an internal cavity of base portion 21 are also disclosed in detail in each of U.S. Pat. No. 10,335,201, titled Spinal Implant System and Methods of Use; and U.S. Pat. No. 10,653,455 titled Spinal Implant System and Methods of Use; U.S. application Ser. No. 17/167,258, titled Instrument for locking Orthopedic Screws, which are all incorporated herein by reference in their entireties. Additionally, spinal implant system 100 may include a rod clamp 30 which may be disposed within passageway 22, for example. Rod clamp 30 may have a toroidal shape in a perspective view (see FIG. 5) and in a cross section view may have a C-shape having a cutout portion, for example. Additionally, in various embodiments passageway 22 may include various contours that facilitate the positioning of rod clamp 30. Furthermore, rod clamp 30 may include a rim portion 31 at the front and back sides thereof, for example. Rim portion 31 may facilitate the positioning of rod clamp 30 in a central position within passageway 22, for example. Additionally, and due in part to the toroidal shape of rod clamp 30, in various embodiments rod clamp 30 may allow a rod 40 positioned therein to modestly move in the lateral direction and vertical direction about 5 degrees to about 10 degrees, for example. This may be particularly advantageous when installing rod 40 and/or contouring rod 40 into a particular alignment after bone screws 10 have been installed. For example, in some surgical settings, it may only be possible to install bone screws 10 in a specific location and allowing some maneuverability of rod 40 via rod clamp 30 may assist the final positioning and/or internal loading of the final construct. In other embodiments (not illustrated), rod clamp 30 is designed to prevent the aforementioned modest movement. Once nut 50 is sufficiently tightened, rod clamp 30 may compress and provide a clamping force against rod 40, for example.

FIGS. 7A and 7B are side cross section views of a spinal implant system 100. In the example illustrations, the first and second implant receivers 20 are securely coupled to bone screws 10. For example, a surgeon may couple the first and second implant receivers 20 to respective bone screws 10 by pushing each of implant receivers 20 down against the bone screw 10 by, e.g., an instrument for locking orthopedic screws. In various embodiments, a surgeon may push down on each implant receiver 20 simultaneously and in other embodiments, a surgeon may push down on each implant receiver 20 in sequence. For example, a surgical instrument may push implant receiver 20 down such that the upper and lower rings 8, 9 are seated around the head portion 11 of bone screw 10 and nested within and retained by corresponding cavities 8a, 9a of lower base portion 21, for example Thereafter, a surgeon may rotate crown 2 such that outer threads 4 engage with corresponding threads 25 of the lower portion 21 of implant receiver 20 and the crown 2 advances downward in the vertical direction (X direction). As the crown 2 advances, the head portion 11 of screw 10 may be firmly seated within lower cavity 6 of crown 2. In various embodiments, lower cavity 6 may resemble a hemispherical shape or dome shape and/or be shaped like a hemisphere or dome corresponding to the hemispherical or dome shaped head portion 11 of a bone screw 10, for example.

In seating upper and lower rings 8, 9 in corresponding cavities 8a, 9a implant receivers 20 may be secured to bone screws 10. Although the discussion and illustrations herein are framed and illustrated in the context of uniaxial bone screws, it is contemplated that in some embodiments, at least one of the first and second bone screws 10 may be configured as multi-axial screws, sagittal angulation screws, pedicle screws, mono-axial screws, uni-planar screws, fixed screws, anchors, tissue penetrating screws, conventional screws, expanding screws. For example, either of implant receivers 20 may be coupled to a bone screw 10 at an angle. In some embodiments, bone screws 10 may be employed with wedges, anchors, buttons, clips, snaps, friction fittings, compressive fittings, expanding rivets, staples, nails, adhesives, posts, connectors, fixation plates and/or a post, to name a few possible example configurations.

Once implant receiver 20 is securely coupled to bone screw 10, a surgeon may tighten the nut 50. The interior thread pattern of nut 50 may engage with the exterior thread pattern 4 of crown 2 and the nut 50 may advance downward in the vertical direction (X direction). As the nut 50 advances, the upper portion 23 and lower portion 21 are brought closer together thereby closing the C shaped portion of arm 29. As the C shaped portion closes, a compressive force is applied to the rod clamp 30 and rod 40. After the nut 50 is sufficiently tightened, the rod clamp 30 and rod 40 may be retained in place relative to implant receiver 20 in the horizontal, lateral, and vertical directions, for example.

FIG. 8 is a perspective view of an alternate rod 45 for use with disclosed spinal implant systems 100. At least one advantage of rod 45 may be that end caps 46 prevent rod 45 from sliding out of and/or uncoupling from the first and second receivers 20, for example Additionally, by utilizing rod 45, a spinal implant system 100, or at least a portion thereof, may be pre-assembled before commencing a surgery at a manufacturing facility and/or on site during pre-operative planning. However, other systems may be pre-assembled and rely on rod 40, rather than rod 45, for example Another advantage of delivering a pre-assembled spinal implant system 100 is that a surgeon may relatively quickly secure the pre-assembled spinal implant system 100 to a pair of adjacent vertebrae of a patient, for example. Furthermore, in various embodiments rod 45 (or rod 40) may be pre-contoured for patient specific anatomy and/or a patient specific procedure, for example.

Figure 9:
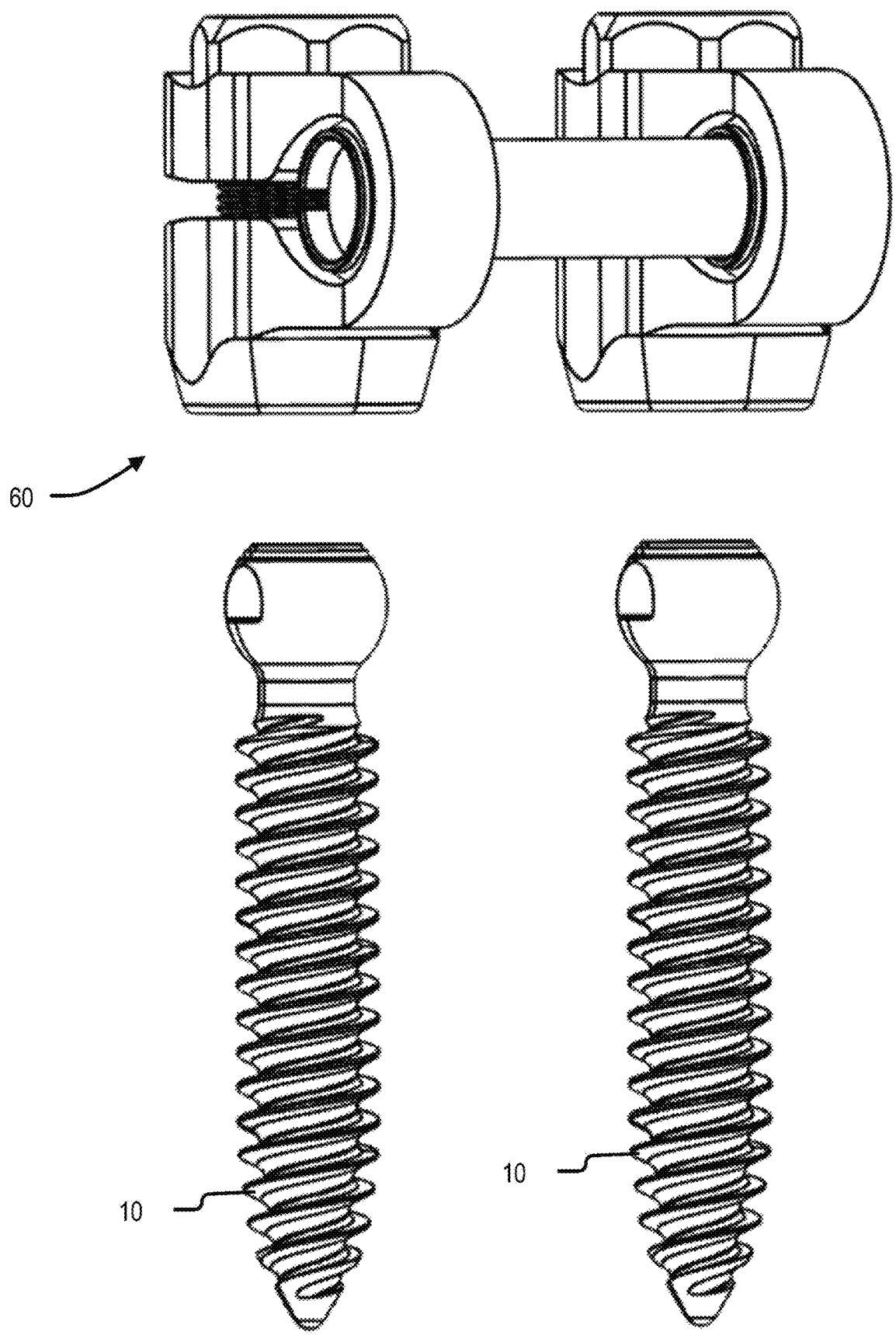
FIG. 9 is side view of a pre-assembled portion of a spinal implant system before being securely coupled to a pair of bone screws.
Figure 10:
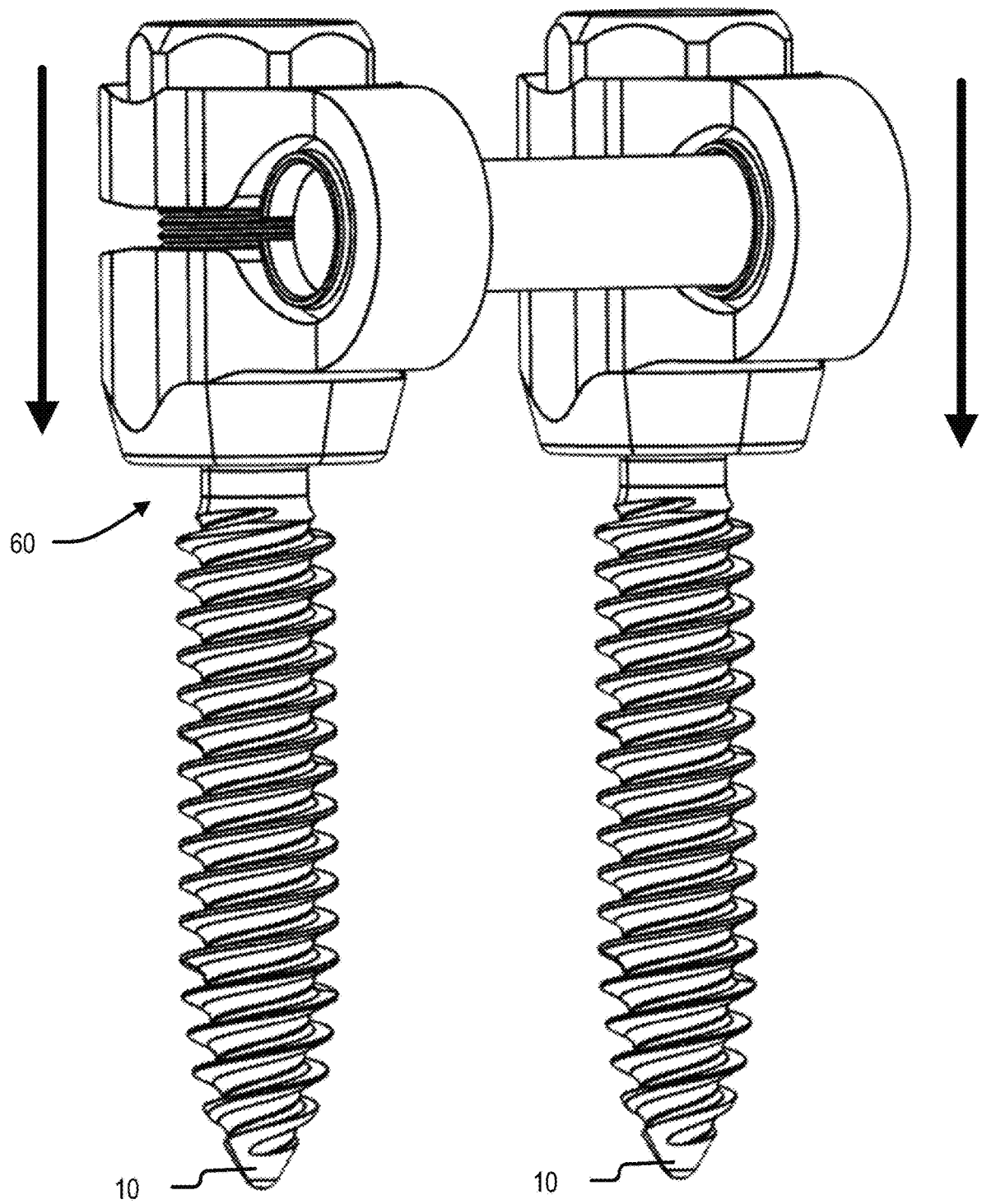
FIG. 10 is side view of the pre-assembled portion of a spinal implant system after being securely coupled to a pair of bone screws.
Figure 11:
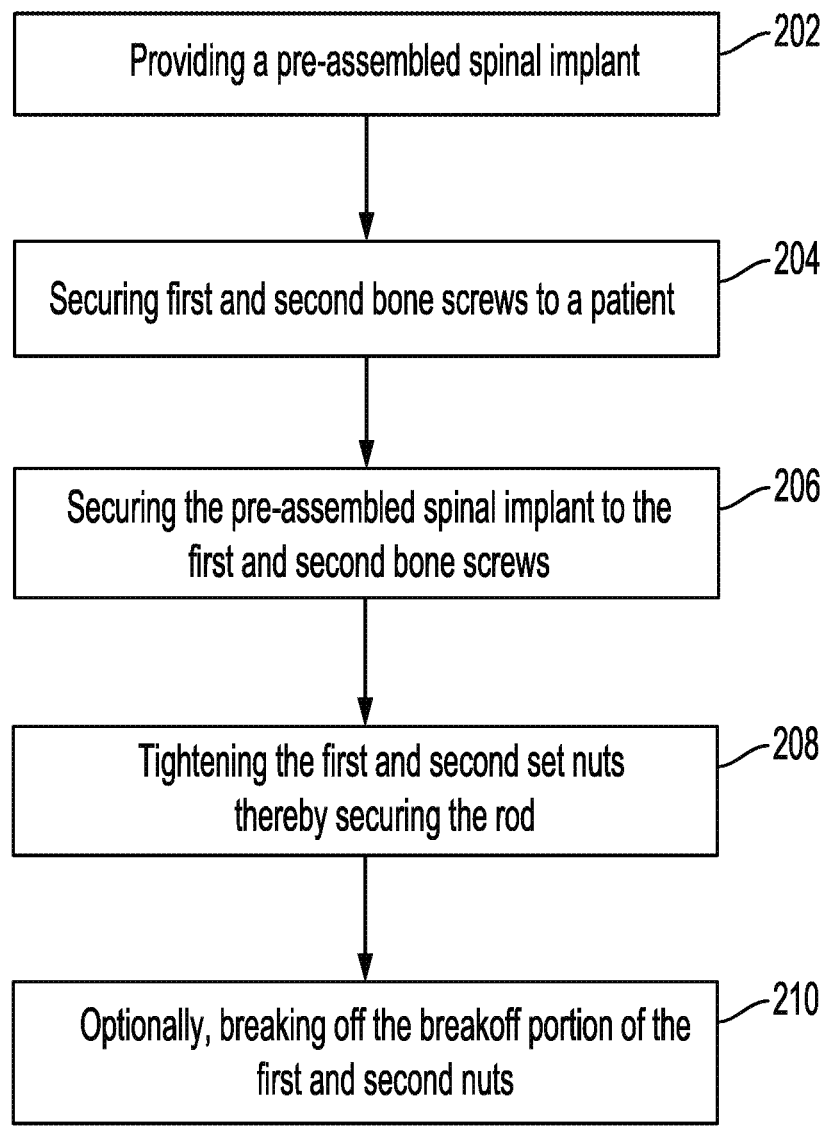
FIG. 11 is a flow chart of an example method of use of disclosed spinal implant embodiments.

FIGS. 9 and 10 are side views of a pre-assembled spinal implant 60. As shown in FIG. 9, a rod 40 is secured within the passageways 22 of first and second implant receivers 20, for example. As explained above, rod 40 may be substituted for rod 45 in some embodiments. Rod 40 may be securely retained within passageways 22 due to first and second nuts 50 being sufficiently tightened such that the upper portion 23 and lower portion 21 are brought closer together thereby providing a clamping force against rod 40. In the example embodiment, spinal implant 60 is pre-assembled and the nuts 50 and crown 2 are finger tightened against the illustrated components. As shown in FIG. 10, an end user such as a surgeon may push down against the first and second implant receivers 20 simultaneously such that the head portion 11 of each of the bone screws 10 is securely coupled to the corresponding implant receiver 20 as explained above, for example.

FIG. 11 is an example flow chart of a method 200 of installation of a pre-assembled spinal implant 60. The following discussion of method 200 may include reference to components, features, and functionality of spinal implant system 100 as explained above for context, however, the method as disclosed below is not limited to the specific spinal implant system 100 embodiments disclosed above. At step 202, a spinal implant system may be provided, for example pre-assembled spinal implant 60 of spinal implant system 100 or the like. At step 204, a first bone screw 10 or fastener and a second bone screw 10 or fastener may be secured to a patient's anatomy, for example, a pair of bone screws 10 may be secured to adjacent vertebrae of a patient. At step 206, the pre-assembled spinal implant 60 may be secured to the first and second bone screws 10. In various embodiments, the pre-assembled spinal implant 60 may be aligned at an angle relative to an extension direction of bone screws 10. In various embodiments, the pre-assembled spinal implant 60 may be initially coupled to first and second bone screws 10 by pushing down on spinal implant 60. For example, as shown in FIG. 10, the first and second implant receivers 20 are secured to the first and second bone screws 10 by pushing down on the first and second implant receivers 20. For example still, each implant receiver 20 may be secured to a corresponding bone screw 10 by pushing implant receiver 20 downward and seating various locking rings 8, 9 around the head portion 11 of bone screw 10 and within various receiving cavities 8a, 9a, of implant receiver 20 as explained above. In some embodiments, the first and second implant receivers 20 may be secured to the first and second bone screws simultaneously by, for example, a pair of reduction instruments similar to the rod-reducing instrument described in U.S. Pat. No. 6,790,209, titled Rod Reducer Instruments and Methods, the entire contents of which are incorporated herein in their entirety. Additionally, the crown 2 may be rotated such that the head portion 11 of bone screw 10 is secured within a lower cavity of crown 2. At step 208, a rod 40 (or rod 45) may be secured in a final position by sufficiently tightening the first and second nuts 50. For example, the first and second nuts 50 may be rotated by a driver instrument such as a wrench or socket and nuts 50 may advance downward along vertical axis A-A such that the upper portion 23 and lower portion 21 are brought closer together thereby retaining rod 40 in place by a compressive force. In some embodiments, a breakoff portion of each of the first and second nuts 50 may be broken off. For example, a breakoff portion of either of nuts 50 may be broken off by a breakoff instrument such as the instruments disclosed in U.S. application Ser. No. 17/104,897, titled Combination Set Screw Breakoff and Tab Breaker Instrument, for example.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An implant, comprising:
a first implant receiver having a first upper portion and a first lower portion connected together by a first arm, the first upper portion and first lower portion defining a first longitudinal passageway extending through the first upper portion and first lower portion in a longitudinal direction, the first arm defining a first rod passageway extending in a lateral direction;
a second implant receiver having a second upper portion and a second lower portion connected together by a second arm, the second upper portion and second lower portion defining a second longitudinal passageway extending through the second upper portion and second lower portion in the longitudinal direction, the second arm defining a second rod passageway extending in the lateral direction;
a first crown having a first outside thread pattern extending along an outside circumferential surface of the first crown and having a size and shape corresponding to a size and shape of the first longitudinal passageway;
a second crown having a second outside thread pattern extending along an outside circumferential surface of the second crown and having a size and shape corresponding to a size and shape of the second longitudinal passageway;
a first nut having a first inside thread pattern extending along an inside circumferential surface of the first nut and having a size and shape corresponding to a size and shape of the first outside thread pattern;
a second nut having a second inside thread pattern extending along an inside circumferential surface of the second nut and having a size and shape corresponding to a size and shape of the second outside thread pattern;
a rod extending in the lateral direction through the first and second rod passageways;
at least one ring configured to secure a head portion of a bone screw within the first lower portion of the first implant receiver or the second lower portion of the second implant receiver when a pushing force is applied to the first or second implant receiver in a direction towards the bone screw;

wherein, in a non-tightened position, the rod may freely move in the lateral direction through the first and second rod passageways, and wherein, in a tightened position, the first nut and second nut are threadably engaged with the first crown and second crown, respectively, and the first arm and second arm contact and constrain the rod from moving in the lateral direction and/or longitudinal direction.

2. The implant of claim 1, wherein:
the first implant receiver includes a first base portion for coupling to a first bone screw, and
the second implant receiver includes a second base portion for coupling to a second bone screw.

3. The implant of claim 2, comprising:
a first rod clamp having a toroidal shape and a second rod clamp having a toroidal shape, and
wherein the first rod clamp is disposed within the first rod passageway and the second rod clamp is disposed within the second rod passageway, and
wherein the rod extends through an interior of the first rod clamp and an interior of the second rod clamp.

4. The implant of claim 3, wherein at least one of the first crown and second crown is configured to provide uni-axial movement.

5. The implant of claim 4, wherein, in a top down view, the rod extends in the lateral direction such that the rod is disposed on a side of the first bone screw and second bone screw.

6. The implant of claim 1, wherein:
the first arm comprises a C-shape connecting the first upper portion and the first lower portion,
the second arm comprises a C-shape connecting the second upper portion and the second lower portion.

7. The implant of claim 1, wherein:
the first lower portion comprises a first lower thread pattern defining a portion of the first longitudinal passageway, and
the second lower portion comprises a second lower thread pattern defining a portion of the second longitudinal passageway.

8. The implant of claim 1, wherein the first and second implant receivers, the first and second crowns, the first and second nuts, and the rod are all pre-assembled in a finger tight position.

9. The implant of claim 1, wherein the rod comprises a first endcap and a second endcap.

10. The implant of claim 9, wherein a size of the first endcap is greater than a size of the first rod passageway and a size of the second endcap is greater than a size of the second rod passageway.

11. The implant of claim 1, wherein the at least one ring is sized and shaped to be seated within an internal cavity formed in the first lower portion of the first implant receiver or the second lower portion of the second implant receiver.

12. The implant of claim 11, wherein the at least one ring is sized and shaped to also be seated around the head portion of the bone screw.

13. The implant of claim 1, wherein, in a cross section view, the rod comprises a circular shape.

14. The implant of claim 13, wherein the first and second rod passageways comprise a circle shape, respectively.

15. A method for installing a spinal implant, comprising:
providing a pre-assembled implant, comprising:
a first implant receiver having a first upper portion and a first lower portion connected together by a first arm, the first upper portion and first lower portion defining a first longitudinal passageway extending through the first upper portion and first lower portion in a longitudinal direction, the first arm defining a first rod passageway extending in a lateral direction;
a second implant receiver having a second upper portion and a second lower portion connected together by a second arm, the second upper portion and second lower portion defining a second longitudinal passageway extending through the second upper portion and second lower portion in the longitudinal direction, the second arm defining a second rod passageway extending in the lateral direction;
a first crown having a first outside thread pattern extending along an outside circumferential surface of the first crown and having a size and shape corresponding to a size and shape of the first longitudinal passageway;
a second crown having a second outside thread pattern extending along an outside circumferential surface of the second crown and having a size and shape corresponding to a size and shape of the second longitudinal passageway;
a first nut having a first inside thread pattern extending along an inside circumferential surface of the first nut and having a size and shape corresponding to a size and shape of the first outside thread pattern;
a second nut having a second inside thread pattern extending along an inside circumferential surface of the second nut and having a size and shape corresponding to a size and shape of the second outside thread pattern;
a rod extending in the lateral direction through the first and second rod passageways; and
at least one ring configured to secure a head portion of a bone screw within the first lower portion of the first implant receiver or the second lower portion of the second implant receiver when a pushing force is applied to the first or second implant receiver in a direction towards the bone screw;
securing first and second bone screws to a patient; and
securing the pre-assembled spinal implant to the first and second bone screws.

16. The method of claim 15, further comprising:
tightening the first nut such that the first nut advances along the first crown and compresses the first upper portion and first lower portion together thereby tightening the rod within the first rod passageway; and
tightening the second nut such that the second nut advances along the second crown and compresses the second upper portion and second lower portion together thereby tighten the rod within the second rod passageway.

17. The method of claim 15, wherein securing the pre-assembled spinal implant to the first and second bone screws further comprises orienting the pre-assembled spinal implant such that, in a top down view, the rod is oriented on the side of the first bone screw and second bone screw.

18. The method of claim 17, further comprising:
constraining the rod in the longitudinal direction and in a lateral direction perpendicular to the longitudinal direction, and
preventing the rod from sliding out of the first passageway and second passageway in a lateral direction perpendicular to the longitudinal direction and the lateral direction.

19. The method of claim 17, wherein the securing the pre-assembled spinal implant to the first and second bone screws step further comprises simultaneously securing the first implant receiver to the first bone screw and the second implant receiver to the second bone screw.

\* \* \* \* \*